US006202493B1

(12) United States Patent
Cantrall et al.

(10) Patent No.: US 6,202,493 B1
(45) Date of Patent: **\*Mar. 20, 2001**

(54) METHODS AND APPARATUS FOR DETERMINING A FIRST PARAMETER(S) OF AN OBJECT

(75) Inventors: Christopher Joseph Cantrall, Normanhurst; Barry Victor Holcombe, Hunters Hill; Graham John Higgerson, Winston Hills; Roger Neil Caffin, Berrilee; William Humphries, North Epping, all of (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 0 days.

This patent is subject to a terminal disclaimer.

(21) Appl. No.: 09/236,476

(22) Filed: Jan. 25, 1999

Related U.S. Application Data

(62) Continuation of application No. 08/955,491, filed on Oct. 22, 1997, now Pat. No. 5,915,279, which is a continuation of application No. 08/732,333, filed as application No. PCT/AU95/00250 on Apr. 27, 1995, now abandoned.

(30) Foreign Application Priority Data

Apr. 27, 1994 (AU) .................................................. PM5330

(51) Int. Cl.$^7$ ...................................................... G01L 1/24
(52) U.S. Cl. .............................................................. 73/800
(58) Field of Search ............................ 73/160, 800, 826, 73/827, 828; 356/238; 250/559.11

(56) References Cited

U.S. PATENT DOCUMENTS 4,330,062  5/1982  Conway et al. .
4,577,104  3/1986  Sturm .

(List continued on next page.)

FOREIGN PATENT DOCUMENTS 37 06 056  5/1988  (DE) .
3706 056   5/1998  (DE) .

(List continued on next page.)

OTHER PUBLICATIONS

"Corolab 7F for Foreign Fibre Detection", Schlafhorst Motor Spinning Systems.
Derwent Abstract Accession No. 84–022317/04, SU 1.

*Primary Examiner*—Max Noori
(74) *Attorney, Agent, or Firm*—Pillsbury Madison & Sutro LLP

(57) ABSTRACT

A method and apparatus for determining a first parameter(s) of an object is disclosed. The apparatus includes means for locating the object (101), in a measurement interaction volume(s) (150, 151, 152, 153), a light absorbing background (100), operatively associated with the measurement interaction volume(s), at least one light source (120), for passing a measurement light beams(s) through the measurement interaction volume(s) to interact with the object (101), to produce measurement outgoing light, the measurement light beam(s) comprising at least two spectrally different wavelengths of light, at least one detector (108, 109, 110), to detect the at least two measurement spectrally different outgoing light portions (105, 106, 107) and to general signals therefrom, whereby the signals are a function of the first parameter(s), the detector(s) (105, 106, 107) being operatively associated with the light source, means for filtering the measurement outgoing light (102, 103, 104) from the measurement interaction volume(s0 into at least two measurement spectrally different outgoing light portions (105, 106, 107), the means for filtering being operatively associated with the light source(s) and/or the at least one detector, and means for determining the first parameter(s) from the signals (125), the means for determining being operatively associated with the detector.

12 Claims, 13 Drawing Sheets

U.S. PATENT DOCUMENTS

| | | |
|---|---|---|
| 4,737,648 | 4/1988 | Smith et al. . |
| 4,739,176 | 4/1988 | Allen et al. . |
| 4,928,013 | 5/1990 | Howarth et al. . |
| 4,948,260 | 8/1990 | Felix et al. . |
| 5,229,841 | 7/1993 | Taranowski et al. . |
| 5,383,017 | 1/1995 | Schürch . |
| 5,530,551 | 6/1996 | Cantrall et al. . |
| 5,915,279 * | 6/1999 | Cantrall et al. .................. 73/800 |

FOREIGN PATENT DOCUMENTS

| | | |
|---|---|---|
| 197763 | 10/1986 | (EP) . |
| 226843 | 7/1987 | (EP) . |
| 399 45 A2 | 11/1990 | (EP) . |
| 553 446 A2 | 8/1993 | (EP) . |
| 652 432 A1 | 5/1995 | (EP) . |
| 2187281 | 9/1987 | (GB) . |
| 143830 | 2/1989 | (PL) . |
| 1004-878 | 3/1983 | (SU) . |
| 1086-371 | 4/1984 | (SU) . |
| 82/03688 | 10/1982 | (WO) . |
| 93/13407 | 7/1993 | (WO) . |
| 93/15389 | 8/1993 | (WO) . |

* cited by examiner

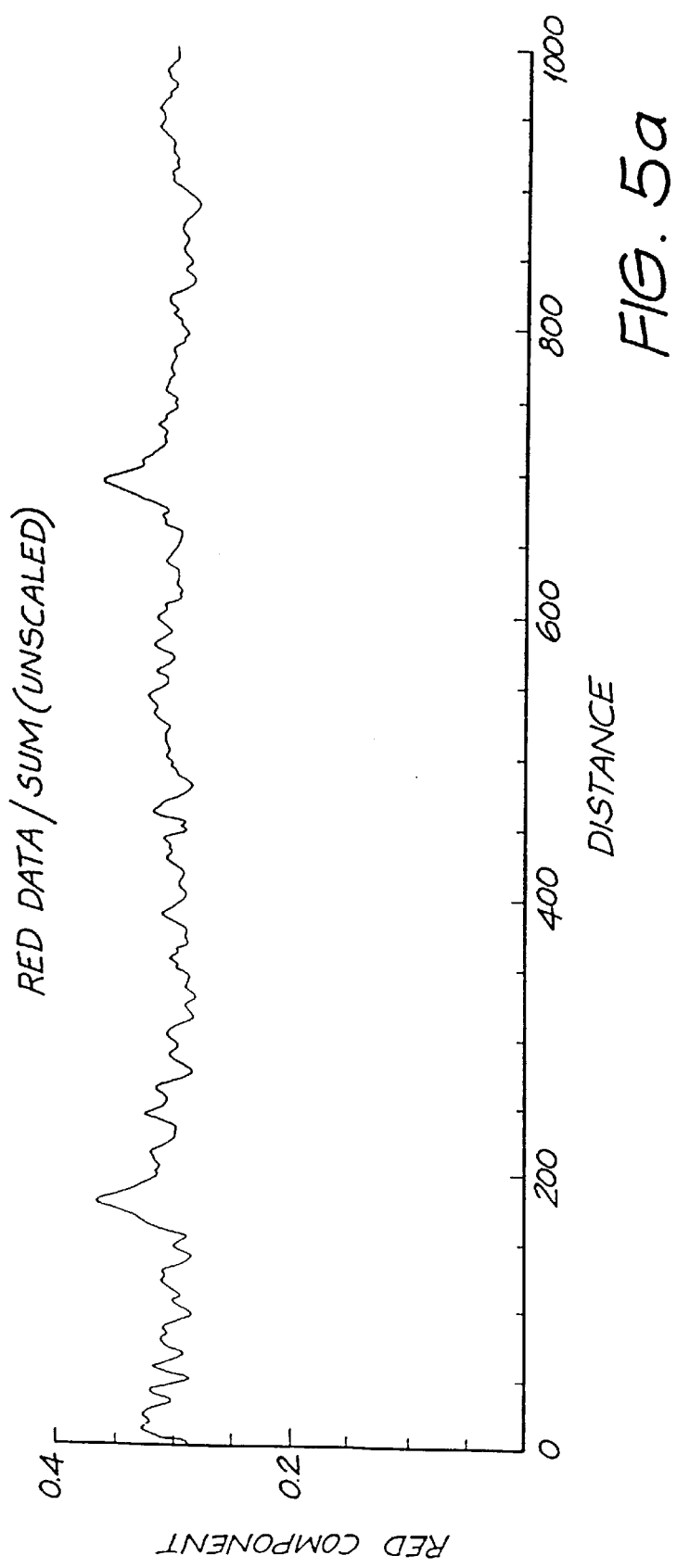

METHODS AND APPARATUS FOR DETERMINING A FIRST PARAMETER(S) OF AN OBJECT

This application is a continuation of application Ser. No. 08/955,491, filed Oct. 22, 1997 U.S. Pat. No. 5,915,279, which was a continuation of application Ser. No. 08/732,333 filed Oct. 28, 1996, now abandoned, which claimed the benefit of the national phase of International Application No. PCT/AU95/00250, filed Apr. 27, 1995, which designated the U.S.

TECHNICAL FIELD

The present invention relates to methods for determining at least a first parameter of an object, apparatus for determining at least a first parameter of an object, methods for determining a first parameter which is a function of at least one parameter selected from the group consisting of the diameter of a yarn, the diameter of a fibrous object, the colour of a fibrous object and the colour of a yarn, and apparatus for determining at least a first parameter which is a function of at least one parameter selected from the group consisting of the diameter of a yarn, the diameter of a fibrous object, the colour of a fibrous object and the colour of a yarn.

BACKGROUND ART

There is a need for a method and apparatus which can detect faults, contamination and/or variations in objects especially in fibres or yarns.

OBJECTS OF THE INVENTION

Objects of the present invention are to provide methods for determining at least a first parameter of an object, apparatus for determining at least a first parameter of an object, methods for determining at least a first parameter which is a function of at least one parameter selected from the group consisting of the diameter of a yarn, the diameter of a fibrous object, the colour of a fibrous object and the colour of a yarn, and apparatus for determining at least a first parameter which is a function of at least one parameter selected from the group consisting of the diameter of a yarn, the diameter of a fibrous object, the colour of a fibrous object and the colour of a yarn.

DISCLOSURE OF THE INVENTION

According to a first embodiment of this invention there is provided a method for determining at least a first measurement parameter of an object, comprising:
(a) locating the object in a measurement interaction volume having a light absorbing background;
(b) passing a measurement light beam through the measurement interaction volume, said measurement light beam comprising at least two spectrally different wavelengths of light;
(c) interacting the measurement light beam with the object to produce measurement outgoing light;
(d) filtering the measurement outgoing light from the measurement interaction volume into at least two measurement spectrally different outgoing light portions;
(e) detecting the at least two measurement spectrally different outgoing light portions and generating signals therefrom whereby the signals are a function of the at least first parameter; and
(f) determining the at least first parameter from the signals.

Step (a) may be performed before, at the same time or after step (b).

Typically the light absorbing background is a black background which may be a flat matt black background.

Typically the object is selected from the group consisting of a yarn and a fibrous object, wherein:
step (a) comprises locating the object in a measurement interaction volume having a light absorbing background which is a black background;
step (c) comprises interacting the measurement light beam with the object to produce measurement outgoing light reflected from the object; and
step (d) comprises filtering the reflected measurement outgoing light from the measurement interaction volume into at least two measurement spectrally different outgoing light portions.

Alternatively:
step (d) comprises filtering at least two different portions of the measurement outgoing light into at least two spectrally different wavelength bands;
step (e) comprises detecting the at least two measurement spectrally different wavelength bands, each band being detected by a different detector at the same time or at different times or by the same detector at different times, and generating signals therefrom whereby the signals are a function of the at least first parameter.

In another alternative:
step (d) comprises filtering at least two different portions of the measurement outgoing light into at least two spectrally different wavelength bands; and
step (e) comprises detecting the at least two measurement spectrally different wavelength bands, each band being detected by a different detector at the same time or at different times or by the same detector at different times, and generating signals therefrom whereby the signals are a function of the first parameter.

Advantageously:
step (a) comprises locating the object in a measurement interaction volume having a light absorbing background.

The filtering is typically selected from the group consisting of spectral filtering and temporal filtering.

The method of the invention may further comprise:
(g) outputting at least a first parameter signal which is a function of the at least first parameter.

In one form of the invention:
step (e) comprises detecting at least two measurement spectrally different outgoing light portions and generating signals therefrom which are related to the respective intensities of the at least two measurement spectrally different outgoing light portions whereby the signals are a function of the at least first parameter; and
step (f) comprises determining the at least first parameter from the signals by comparing the signals with reference signals or reference values. The method of the invention may further comprise:
(f') determining from the at least first parameter whether the object is an acceptable object or an unacceptable object.

According to a further embodiment of this invention there is provided a method for determining at least a first parameter of an object, comprising:
(a) locating the object in a measurement interaction volume having a light absorbing background;
(b) passing a measurement light beam through the measurement interaction volume;

(c) interacting the measurement light beam with the object to produce measurement outgoing light;
(d) filtering the measurement outgoing light from the measurement interaction volume into at least two measurement spectrally different outgoing light portions;
(e) detecting the at least two measurement spectrally different outgoing light portions and generating signals therefrom whereby the signals are a function of the at least first parameter; and
(f) determining the at least first parameter from the signals.

Step (a) can be performed before, at the same time or after step (b).

According to another embodiment of this invention there is provided a method for determining at least a first parameter which is a function of at least one parameter selected from the group consisting of the diameter of a yarn, the diameter of a fibrous object, the colour of a fibrous object and the colour of a yarn, comprising:
(a) locating the fibre in a measurement interaction volume having a black light absorbing background;
(b) passing a measurement light beam through the measurement interaction volume;
(c) interacting the measurement light beam with the object to produce measurement outgoing light reflected from the fibre;
(d) filtering the reflected measurement outgoing light from the measurement interaction volume into at least two measurement spectrally different outgoing light portions;
(e) detecting the at least two measurement spectrally different outgoing light portions and generating signals therefrom whereby the signals are a function of at least one parameter selected from the group consisting of the diameter of the fibre and the colour of the fibre; and (f) determining from the signals at least a first parameter which is a function of the at least one parameter.

This embodiment may further include:
(g) outputting at least a first parameter signal which is a function of the at least first parameter.

According to another embodiment of this invention there is provided a method for determining at least a first parameter of an object, comprising:
(a) locating the object in a measurement interaction volume having a light absorbing background;
(b) passing a measurement light beam through the measurement interaction volume;
(c) interacting the measurement light beam with the object to produce measurement outgoing light;
(d) detecting the measurement outgoing light from the measurement interaction volume and generating at least two different measurement signals therefrom, each of said signals corresponding to a spectrally different portion of the measurement outgoing light, whereby the signals are a function of the at least first parameter;
(e) determining the at least first parameter from the signals Step (a) can be performed before, at the same time or after step (b).

According to another embodiment of this invention there is provided a method for determining at least a first parameter which is a function of at least one parameter selected from the group consisting of the diameter of a yarn, the diameter of a fibrous object, the colour of a fibrous object and the colour of a yarn, comprising:
(a) locating the fibre in a measurement interaction volume having a black light absorbing background;
(b) passing a measurement light beam through the measurement interaction volume;
(c) interacting the measurement light beam with the object to produce measurement outgoing light reflected from the fibre;
(d) detecting the measurement outgoing light from the measurement interaction volume and generating at least two different measurement signals therefrom, each of said signals corresponding to a spectrally different portion of the measurement outgoing light, whereby the signals are a function of at least one parameter selected from the group consisting of the diameter of the fibre and the colour of the fibre; and
(e) determining from the signals a first parameter which is a function of the at least one parameter.

The latter method may further include:
(f) outputting a first parameter signal which is a function of the first parameter.

According to a second embodiment of this invention there is provided an apparatus for determining a first parameter of an object, comprising:
(a) means for locating the object in a measurement interaction volume;
(b) a light absorbing background operatively associated with the measurement interaction volume;
(c) at least one light source for passing a measurement light beam through the measurement interaction volume to interact with the object to produce measurement outgoing light, the measurement light beam comprising at least two spectrally different wavelengths of light;
(d) at least one detector to detect the at least two measurement spectrally different outgoing light portions and to generate signals therefrom, whereby the signals are a function of the first parameter, the detector being operatively associated with the light source;
(e) means for filtering the measurement outgoing light from the measurement interaction volume into at least two measurement spectrally different outgoing light portions, the means for filtering being operatively associated with the light source and/or the at least one detector; and
(f) means for determining the first parameter from the signals, the means for determining being operatively associated with the detector.

Typically the light absorbing background is a black background which may be a flat matt black background.

Typically:
there at least two detectors, to enable each measurement spectrally different outgoing light portion to be detected by a different detector at the same time or at different times, and generating signals therefrom whereby the signals are a function of the at least first parameter. Typically the means for filtering is selected from the group consisting of means for spectral filtering and means for temporal filtering.

The apparatus may further comprise:
(g) means for outputting at least a first parameter signal which is a function of the at least first parameter the means for outputting being operatively associated with means for determining the at least first parameter.

The apparatus may further comprise:
(f') means for determining from the first parameter whether the object is an acceptable object or an unacceptable object, the means for determining being operatively associated with the means for determining the at least first parameter.

According to another embodiment of this invention there is provided an apparatus for determining at least a first parameter of an object, comprising:
(a) means for locating the object in a measurement interaction volume;
(b) a light absorbing background operatively associated with the measurement interaction volume;
(c) a light source for passing a measurement light beam through the measurement interaction volume to interact with the object to produce measurement outgoing light;
(d) means for filtering the measurement outgoing light from the measurement interaction volume into at least two measurement spectrally different outgoing light portions, the means for filtering being operatively associated with the light source;
(e) a detector to detect the at least two measurement spectrally different outgoing light portions and to generate signals therefrom, whereby the signals are a function of the first parameter, the detector being operatively associated with the means for filtering; and
(f) means for determining the first parameter from the signals, the means for determining being operatively associated with the detector.

The measurement light beam may be focused or unfocused.

According to a further embodiment of the invention there is provided an apparatus for determining a first parameter which is a function of at least one parameter selected from the group consisting of the diameter of a yarn, the diameter of a fibrous object, the colour of a fibrous object and the colour of a yarn, comprising:
(a) means for locating the fibre in a measurement interaction volume having a black light absorbing background;
(b) a light source for passing a measurement light beam through the measurement interaction volume to interact with the fibre to produce measurement outgoing light reflected from the fibre;
(c) means for filtering the reflected measurement outgoing light from the measurement interaction volume into at least two measurement spectrally different outgoing light portions, the means for filtering being operatively associated with the light source;
(d) a detector to detect the at least two measurement spectrally different outgoing light portions and to generate signals therefrom whereby the signals are a function of at least one parameter selected from the group consisting of the diameter of the fibre and the colour of the fibre the detector being operatively associated with the means for filtering; and
(e) means for determining from the signals a first parameter which is a function of at least one parameter, the means for determining being operatively associated with the detector.

This apparatus may further include:
(f) means for outputting a first parameter signal which is a function of the first parameter.

According to another embodiment of this invention there is provided an apparatus for determining a first parameter of an object, comprising:
(a) means for locating the object in a measurement interaction volume;
(b) a light absorbing background operatively associated with the measurement interaction volume;
(c) a light source for passing a measurement light beam through the measurement interaction volume to interact with the object to produce measurement outgoing light;
(d) a detector to detect the measurement outgoing light from the measurement interaction volume and for generating at least two different measurement signals therefrom, each of said signals corresponding to a spectrally different portion of the measurement outgoing light, whereby the signals are a function of the first parameter, the detector being operatively associated with the light source; and
(e) means for determining the first parameter from the signals, the means for determining being operatively associated with the detector.

According to a further embodiment of the invention there is provided an apparatus for determining a first parameter which is a function of at least one parameter selected from the group consisting of the diameter of a yarn, the diameter of a fibrous object, the colour of a fibrous object and the colour of a yarn, comprising:
(a) means for locating the fibre in a measurement interaction volume having a black light absorbing background;
(b) a light source for passing a measurement light beam through the measurement interaction volume to interact with the fibre to produce measurement outgoing light reflected from the fibre;
(c) a detector to detect the measurement outgoing light from the measurement interaction volume and for generating at least two different measurement signals therefrom, each of said signals corresponding to a spectrally different portion of the measurement outgoing light, whereby the signals are a function of at least one parameter selected from the group consisting of the diameter of the fibre and the colour of the fibre, the detector being operatively associated with the light source; and
(d) means for determining from the signals a first parameter which is a function of the at least one parameter, the means for determining being operatively associated with the detector.

This apparatus may further include:
(e) means for outputting a first parameter signal which is a function of the first parameter.

The measurement light beam may be focused or unfocused.

Typically the first measurement parameter is or is a function of at least one parameter selected from the group consisting of the diameter of a yarn, the diameter of a fibrous object, the colour of a fibrous object and the colour of a yarn. (The first measurement parameter is also referred to more concisely as "the first parameter" in this specification and in the claims).

The object may be a fluid or solid or other form-of matter. Typically the object is a yarn. Examples of objects include mineral objects, such as diamonds and other crystals, organic and inorganic contaminants, fibrous objects, randomly shaped objects, spherical objects or cylindrical objects. Typically the objects are fibrous objects including woven or twisted fibrous objects. The fibrous objects may be synthetic fibres or natural fibres, particularly dyed fibres, a textile product such as a strand, filament or yarn. The fibres or strands may be fibreglass fibres or strands, hessian fibres or strands, nylon fibres or strands, glass fibres or strands, polnosic and polyester fibres or strands, alpaca fibres or strands, silk fibres or strands, jute fibres or strands, flax and cellulose fibres or strands (including paper, recycled paper, corn stalks, sugar cane, wood, wood shavings, bagasse, wood chip, string, regenerated fibres or strands such as viscose, rayon, cuprammonium rayon and cellulose acetate, sisal fibres or strands, carbon fibres or strands, stainless steel fibres or strands, vegetable fibrous material, polyolefin fibres or strands such as polyethylenes and polypropylene, steel fibres or strands, boron fibres or strands, copper fibres or strands, brass fibres or strands, other metal fibres or strands, teflon fibres or strands, dacron fibres or strands, mylar fibres or strands, aluminium fibres or strands, aluminium alloy fibres or strands, polyamide fibres or strands, polyacrylic fibres or strands, or absorbent fibres or strands such as nylon 66, polyacrylonitrile, or polyvinyl alcohol and absorbent types of polyesters or polyacrylics, edible vegetable fibres or strands, such as wheat fibres or strands, or inedible vegetable fibres or strands, such as wood pulp or cotton fibres or strands, animal fibres or strands, such as meat fibres or strands, wool fibres or strands such as wool fibres or strands from sheep, hairs, such as human hairs, goat hairs, cattle hairs, or feathers, yarns including wool and cotton yarns (especially dyed wool, rabbit hair, kangaroo fur, mohair and cotton yarn, string, wire, optical fibres or strands for example.

Typically the object is selected from the group consisting of a fibre and a yarn, and the at least first parameter is selected from the group consisting of the diameter of the fibre, the difference between the diameter of the fibre and the diameter of a reference fibre, the ratio of the instantaneous diameter of the fibre divided by the running average diameter of the fibre, the colour of the fibre, the difference between the colour of the fibre and the colour of a reference fibre, the ratio of the instantaneous colour of the fibre divided by the running average colour of the fibre, the diameter of the yarn, the difference between the diameter of the yarn and the diameter of a reference yarn, the colour of the yarn, the ratio of the instantaneous colour of the yarn divided by the running average colour of the yarn, and the difference between the colour of the yarn and the colour of a reference yarn.

More typically the object is selected from the group consisting of a wool fibre and a wool yarn, and the first parameter is selected from the group consisting of the diameter of the wool fibre, the difference between the diameter of the wool fibre and the diameter of a reference fibre, the ratio of the instantaneous diameter of the wool fibre divided by the running average diameter of the wool fibre, the colour of the wool fibre, the difference between the colour of the wool fibre and the colour of a reference fibre, the ratio of the instantaneous colour of the wool fibre divided by the running average colour of the wool fibre, the diameter of the wool yarn, the difference between the diameter of the wool yarn and the diameter of a reference yarn, the ratio of the instantaneous diameter of the wool yarn divided by the running average diameter of the wool yarn, the colour of the wool yarn, the ratio of the instantaneous colour of the wool yarn divided by the running average colour of the wool yarn, and the difference between the colour of the wool yarn and the colour of a reference yarn.

Typically in the apparatus of the invention the means for determining the first parameter is selected from the group consists of means for determining the diameter of the fibre, means for determining the difference between the diameter of the fibre and the diameter of a reference fibre, means for determining the ratio of the instantaneous diameter of the fibre divided by the running average diameter of the fibre, means for determining the colour of the fibre, means for determining the difference between the colour of the fibre and the colour of a reference fibre, means for determining the ratio of the instantaneous colour of the fibre divided by the running average colour of the fibre, means for determining the diameter of the yarn, means for determining the difference between the diameter of the yarn and the diameter of a reference yarn, means for determining the colour of the yarn, means for determining the ratio of the instantaneous colour of the yarn divided by the running average colour of the yarn, and means for determining the difference between the colour of the yarn and the colour of a reference yarn.

Typically in the apparatus of the invention the means for determining the first parameter is selected from the group consists of means for determining the diameter of the wool fibre, means for determining the difference between the diameter of the wool fibre and the diameter of a reference fibre, means for determining the ratio of the instantaneous diameter of the wool fibre divided by the running average diameter of the wool fibre, means for determining the colour of the wool fibre, means for determining the difference between the colour of the wool fibre and the colour of a reference fibre, means for determining the ratio of the instantaneous colour of the wool fibre divided by the running average colour of the wool fibre, means for determining the diameter of the wool yarn, means for determining the difference between the diameter of the wool yarn and the diameter of a reference yarn, means for determining the ratio of the instantaneous diameter of the wool yarn divided by the running average diameter of the wool yarn, the colour of the wool yarn, means for determining the ratio of the instantaneous colour of the wool yarn divided by the running average colour of the wool yarn, and means for determining the difference between the colour of the wool yarn and the colour of a reference yarn.

The first parameter may be shape, diameter, area, chemical composition, colour, number of parts, thickness, width, absorptivity, reflectivity, fluorescence, surface texture or other surface detail, or surface roughness, or a change in any one of the foregoing, for example. In the case of a fibrous object for example the first parameter may be diameter and/or colour or change therein, for example.

The light source may be coherent, partially coherent or incoherent and can provide a UV light, visible light, infrared light or far infrared light. Generally the light source is polychromatic and emits light of at least two different wavelengths in the range of and including far UV to far IR. Alternatively, at least two different narrow band light sources may be used each narrow band light source emitting light of a wavelength in the range of and including far UV to far IR the wavelength emitted by one of the source being different from the wavelength emitted by the other source.

Examples of light sources include incandescent sources, such as tungsten filament source, vapour lamps such as halogen lamps including sodium and iodine vapour lamps, discharge lamps such as xenon arc lamp and Hg arc lamp, solid state light sources such as photo diodes, super radiant diodes, light emitting diodes (LED, laser diodes, electroluminescent light sources, frequency. doubled lasers, laser light sources including rare gas lasers such as an argon laser, argon/krypton laser, neon laser, helium neon laser, xenon laser and krypton laser, carbon monoxide and carbon dioxide lasers, metal ion lasers such as cadmium, zinc, mercury or selenium ion lasers, lead salt lasers, metal vapour lasers such as copper and gold vapour lasers, nitrogen lasers, ruby lasers, iodine lasers, neodymium glass and neodymium YAG lasers, dye lasers such as a dye laser employing rhodamine 640, Kiton Red 620 or rhodamine 590 dye, and a doped fibre laser. The light source may be a pinhole light source. The light source may comprise an optical fibre, the exit end of which may effectively act as a pinhole source.

Typically light in the wavelength range 390 nm to 800 nm is used as the measurement light beam. The measurement light beam contains least two different wavelengths (typically 2–5 different wavelength band of light either simultaneously or sequentially. For example, the measurement light beam may be white light or broad band light or light having several different wavelength bands. Typically, light having at least three wavelength bands (the measurement light beam typically is provided by a single light source or multiple light source, typically three different wavelength bands selected from the group consisting of a red band, an orange band, a green band, a yellow band, a purple band and a blue band, more typically a red band, a green band and a blue band.

The light beam may be collimated, diverging or converging. The optical fibres may include glass or plastic elements or a combination of these. The light guide can be a single mode or multimode optical fibre. The light guide may be a fibre bundle. Portions of the source and detector light guides may be portions of the same light guide.

The detector may comprise a single detecting element or an array of detecting elements. The detector may comprise an optical fibre coupled to a detecting element.

Examples of the measurement of the outgoing light include:

(a) filtering at least two different portions of the measurement outgoing light into at least two spectrally different wavelength bands, each band being detected by a different detector at the same time or at different times or by the same detector at different times;

(b) filtering at least two different portions of the measurement outgoing light into at least two spectrally different wavelength bands, each band being detected by the same detector at different times.

Examples of light source/filter/detector configurations include:

(i) A single white light source plus three different colour band filters plus three different detectors, each detector detecting a different colour band;

(ii) Three different colour band light sources (e.g., red, green and blue LED plus three different colour band filters (red, green and blue filters) plus three different detectors, each detector detecting a different colour band;

(iii) Three different colour band light sources in time sequence (e.g. red, green and blue LED plus one detector time multiplexed to detect the different colour bands;

(iv) Three different colour band light sources operating at three different frequencies (e.g. red, green and blue LED plus one detector plus three frequency filters to spectrally filter each different colour band and to output signals related thereto plus at least one detector to detect the outputted signals.

(v) A single white light source plus n different colour band filters plus n different detectors, each detector detecting a different colour band, where n is typically 2–20, more typically 2–10 and even more typically 2–5;

(vi) N different colour band light sources (e.g. red, green and blue LED plus n different colour band filters (red, green and blue filters) plus n different detectors, each detector detecting a different colour band, where n is typically 2–20, more typically 2–10 and even more typically 2–5;

(vii) N different colour band light sources in time sequence (e.g. red, green and blue LEDs) plus one detector time multiplexed to detect the different colour bands, where n is typically 2–20, more typically 2–10 and even more typically 2–5; and (viii) N different colour band light sources operating at n different frequencies (e.g. red, green and blue LEDs) plus one detector plus n frequency filters to spectrally filter each different colour band and to output signals related thereto plus at least one detector to detect the outputted signals, where n is typically 2–20, more typically 2–10 and even more typically 2–5.

The apparatus may include means to bass the object through the interaction volume, the means to pass being operatively associated with the means for locating. The means to pass may be a fibre winder such as a yarn (especially wool based yarn) or cotton winder, a sample carrier such as a light absorbing (e.g. black) conveyer strip, a sample holder on a linear stage. The apparatus may comprise a scanner operatively associated with the light source and/or the object and/or the sample carrier to scan the light beam relative to the object in the interaction volume. Alternatively, the object may be scanned relative to the light beam or both the object and light beam may be scanned simultaneously (the measurement may also be one in which neither the object or light beam is scanned relative to one another). The scanner may be a piezo-electric stack, a magnetic core/magnetic coil combination, a mechanical vibrator, an electromechanical vibrator, a mechanical or electromechanical scanning mechanism such as a servomotor, an acoustic coupler electrooptic scanning means or any other suitable means. The light source may include a light deflector located between the source and the interaction volume wherein a portion of the light beam passes through the defector and whereby the detector is operatively associated with the source to alter the shape, size, wavelength, intensity, polarisation, phase, direction of travel or focus of at least a portion of the light beam in the interaction volume.

There may be disposed in the path of the outgoing light between the interaction volume and/or the detector, a second light deflector wherein the outgoing light passes through the second deflector which alters the size, shape, intensity, polarisation, phase, direction of travel, focus for example.

The first and second light deflectors may include light focusers or light reflectors. The focuser may be refractive lenses, including microscope objectives, reflective lenses, and/or holographic optical elements. If the light is of a frequency other than in the range of UV to near infrared light or other types of energies, analogous focusing elements are used in place of the optical focusing elements. The reflector may be a mirror or partially silvered mirror, a beam splitter including a polarisation dependent beam splitter, light waveguide splitter (e.g. an optical fibre coupler) or a wavelength dependent beam splitter, for example. The optical fibre coupler may be a fused biconical taper coupler, a polished block coupler, a bottled and etched coupler or a bulk optics type coupler with fibre entrance and exit pigtails, a planar waveguide device based on photolithographic or ion-diffusion fabrication techniques or other like coupler. The interaction is typically one or a combination of refraction, diffraction, reflection, scattering, fluorescence, stimulated emission, incandescence, shadowing, polarisation rotation, phase retardation and other polarisation effects, occlusion, optical absorption, interference effects, sum frequency generation, one giving rise to a diffraction pattern, refraction, phase alteration, second, third or fourth harmonic generation, difference frequency generation, optical bistability, self bleaching, Raman scattering or Brillouin scattering. A nonlinear reaction can be involved as a result of heating, refractive index change, charge build-up or charge migration.

The measurement outgoing light may be intensity modulated (including spatially or temporally dependent intensity modulation such as intensity peaks or troughs or as or not as a function of time), amplitude, wavelength or frequency modulation, phase, polarisation, wavelength, direction of travel, for example. The detector, the means for determining the at least first parameter, and/or the means for locating may comprise a calculator which may include optical, electrical, optoelectronic, mechanical or magnetic elements, for example, or may include such techniques as optical and/or electrical heterodyning, quadrature operation, Multi area detectors or phase lock loop techniques, for example. The means for determining the at least first parameter may log and analyse a signal from the detector or may log and analyse the first parameter.

The detector may comprise an array of detecting elements and/or apertures. An aperture in the array may be a light entrance portion of an light guide to collect a portion of the outgoing light and guide it to the detector.

A detecting element in the array may be photodiode, photomultiplier, part of a ccd array or the like. The array may be a one or two dimensional array or a planar array. The measurement outgoing light is not occluded light. Typically the measurement outgoing light is light reflected from the object.

Where the first parameter to be measured is diameter, the function measured is a change in amplitude of the entire spectrum of the measurement outgoing light. Where the first parameter to be measured is colour, the function measured is a change in the shape of the spectrum. Some preferred forms of the method and apparatus of the invention rely on the fact that the value of the first parameter of the object being examined is mostly as desired or within a desired range of values so that the frequency of unacceptable first parameter values does not significantly alter the average first parameter value. That is when the diameter of a fibre, strand, yarn, etc. is being measured, for example, the bulk of the fibres are the desired diameter and colour and the major part of each fibres length is the desired diameter or within an acceptable diameter range. The means for determining the first parameter typically includes digital and/or analogue processing. The means for locating may comprise a timer and/or a counter.

Methodology

The method and apparatus of the invention may determine the first parameter by comparison with a known reference or discrimination may be done on a relative basis. The basis for determining parameter variation in an object is as follows.

An object O will typically have a number of measurable parameters pn where n=1, 2, . . . i, . . . k, . . . j. Take, for example, the case where it is desired to measure whether there is a variation in at least one of parameters pn. For parameter pn the intensity of light Ir for a given wavelength or band of wavelengths. X n reflected from O at position x along its length is a function Fn of O and x thus:

$$I_r(\lambda_n) = F_n(0, x) \qquad 1.1$$

In the case of no variation in pn along the length x of O we have:

$$\frac{d}{dx} I_r(\lambda_n) = 0 \qquad 1.2$$

Where the average over length of function F is denoted by: $\bar{F}$ and there is no variation in pn the following obtains:

$$\overline{F_n(0,x)} - I_r(\lambda_n) = \qquad 1.3$$

Hence for no variation in pn:

$$\frac{I_r(\lambda_n)}{\overline{F_n(0, x)}} = 1 \qquad 1.4$$

Where there is variation in pn:

$$\frac{d}{dx} I_r(\lambda_n) \neq 0 \qquad 1.5$$

$$\overline{F_n(0, x)} - I_r(\lambda_n) \neq 0 \qquad 1.6$$

$$\frac{I_r(\lambda_n)}{\overline{F_n(0, x)}} \neq 1 \qquad 1.7$$

Where the object O is being moved through the measurement volume the variable t for time may be substituted for the variable x for position.

It is apparent from equations (1.2)–(1.7) that a conditional test or tests can be applied, if required at this stage, to determine variation in a particular pn, namely, Δpn such as, for example, a test to ascertain whether Δpn is within a desired range or not. One such test may be conducted by comparing lr(λn) for a given measurement with a reference value which may advantageously be a running average based on a temporal average measurement. Alternatively this reference may be based on a spatial average or a fixed reference. There are a number of advantages in using a ruling average based on a temporal measurement namely:

One detector assembly gets signals to set up a reference and measure an instantaneous or point value. There is no need for dual assemblies adaptation and measurement of parameters.

The reference signal generated from a running average will adapt to the parameters normal to the object being measured.

The parameter pn may be a combination of effects at several different wavelengths or bands thus:

$$P_n = \sum_{j=1}^{n} k_{n,j} I_r(\lambda_j) \qquad 1.8$$

where the factors knj are specific to this parameter. The average value of pn is denoted by $\bar{P}_n$.

By comparing pn with $\bar{P}_n$, a conditional test or tests may be applied to ascertain whether Δpl is within a desired range or not.

One particularly advantageous way of determining an average value of F(O,x) is to measure lr(λn) for n number of objects O(pl) . . . O(pn) or for one object O(pi) over a significant length of that object.

One particular embodiment of this invention provides an apparatus to provide a number of signals from an object such as a fibre, for example. These signals are generated by illuminating the fibre and sensing the reflected energy at particular bands of the visible spectrum. These signals may be generated by using light sources of different wavelengths or wavelength bands switched on repeatedly at separate times or in a known pattern of times and detecting the signals with a single detector. This method gives a time series signal that contains the relevant information. This time series signal is then repeatedly sampled and stored at the appropriate times to give a parallel form of data.

An alternative method is to illuminate an object, such as a fibre, with white light or light containing several wavelength bands, from one or more light sources, and sense the energy reflected in the different bands by using a number of detectors with selected filters in front of each detector. This method gives the relevant information in a parallel form. Given the signal in their parallel form, the following relationships can be seen. Let B1,B2 . . . Bn represent the light energy detected in the visible bands 1 to n. The diameter of the fibre is proportional to the sum total of energy sensed in each band if colour is constant or there is not a significant shift in overall colour:

$$\text{Fibre (diameter) reflectivity} \alpha \sum_{j=1}^{n} B_j \qquad 1.9$$

By integrating equation 1.9 over a significant area (or period of time t1 . . . t2) of fibre one can obtain an average value for the fibre which will be related to the "normal" diameter of the fibre. By dividing this normal (average) value into the instantaneous value (1.9) we obtain a signal which is independent of the illumination intensity and fibre diameter (1.10). If the current area being measured is of "normal" diameter then this ratio approximates unity and is stable. If we get an "evenness" variation this ratio will vary from unity by an amount proportional to the size of the diameter variation.

$$\text{(Diameter) Reflectivity Variation} \alpha \left[ \frac{\sum_{j=1}^{n} B_j}{\frac{1}{t_2 - t_1} \int_{t_1}^{t} \sum_{j=1}^{n} B_j \, dt} \right] \qquad 1.10$$

By comparison of this variation to a settable reference an output can be generated that will indicate if an "evenness" fault exists.

In a practical embodiment of this invention there will typically be a finite number of bands used. In a particular application the required sensitivity to detection of colour effects will determine the number of bands (i.e. the higher the resolution of colour that is required the larger the number of different coloured bands that are detected).

By comparing the proportional energy in each band to that in other bands a "signature" of the present colour can be obtained. One example of this is shown in the following relationship for a three band system:

$$\text{Colour} \alpha \frac{B_1}{B_2} + \frac{B_1}{B_3} + \frac{B_2}{B_3} \qquad 1.11$$

By integrating equation 1.11 over a significant area (period of time t1 . . . t2) of fibre one can obtain a value of the "normal" colour of the fibre. By dividing this normal value into the instantaneous value one can obtain a signal which is independent of the illumination intensity and fibre diameter. If the current area being measured is "normal" colour then this ratio approximates unity & is stable. If one gets a colour variation this ratio will vary from unity by an amount proportional to the size of the colour variation:

$$\text{Fiber Colour Reflectivity} \frac{\frac{B1}{B2} + \frac{B1}{B3} + \frac{B2}{B3}}{\alpha \frac{1}{t_z - t_1} \int_{t_1}^{t_z} \left( \frac{B1}{B2} + \frac{B1}{B3} + \frac{B2}{B3} \right) dt} \qquad 1.12$$

By comparison of this variation to a settable reference, an output signal can be generated that will indicate if a colour fault exists.

Another method for analysis of these signals for colour analysis may be done by examination of the ratio of energy in each band to the average or finite integral of the total energy reflected, denoted BRi. For a system using n bands we can get n normalised signals that can be compared to a reference learnt from a running time or space average. For a system using n bands the following equation for BRi can be used:

$$BR_1 \alpha \left[ \frac{B_1}{\frac{1}{t} \int \sum_{j=1}^{n} B_j \, dt} \right] \qquad 1.13$$

After each of these ratios are produced, comparisons can be made to a reference value, which may be a fixed value or a settable proportion of the learnt average. The output of these comparators are combined so a change in any one or more bands will produce a digital signal that can be passed to another apparatus.

When the diameter and colour of a fibre are being measured each of the resultant signals from the detector has the following components embedded in it:

Incident light colour temperature and intensity (undesirable component);
Incident light angle, (undesirable component)
diameter of the fibre being examined;
colour of the fibre being examined.

The signals are ratioed in such a way as to eliminate the undesirable components of the signals and the diameter. This ratio technique allows for a more robust design of the system. Doing spectral analysis gives the potential for greater sensitivity hence more effective detection of colour faults. This method and apparatus of the invention may incorporate the ability to learn the colour and/or diameter signatures of the fibre and adapt to slow variations to the normal colour and/or diameter.

Particular embodiments of the method and apparatus of this invention can determine if the current section of fibre within the apparatus is within tolerance for the following parameters on undyed fibre or dyed fibre:

Fibre diameter for determining 'evenness' or linear density variations.
Visible presence of fibre or other material that has not absorbed the dye or is pigmented or stained to a different colour to that of the undyed fibre and as such is determined to be a contaminant.

This particular method and apparatus can work regardless of the colour of the dye used on the fibre. When a fibre's parameters are determined to be outside tolerance a signal is typically passed to another apparatus which will enable that apparatus to take appropriate action. Typically the tolerance is variable and can be set by external means.

Particular embodiments of the method and apparatus of this invention can determine if the current section of fibre/yarn contains the following:

Differently coloured contaminants and/or foreign bodies in the fibre or yarn including differently coloured foreign fibres.

Differently coloured fibres or yarn in fibre and yarn including differently coloured foreign fibres or foreign yarn.

In the apparatus employing this method the functions Ir(k) are designed to be the energy levels reflected by the yarn in each of the spectral bands of interest. These signals are summed to generate a signal proportional to the diameter of the fibre being measured. By employing a lowpass filter which approximates an definite integral function, a signal proportional to the running average of the fibre being measured is generated. If the assumption is made that the fibre are mostly the correct colour the this running average will learn the correct diameter. By dividing this learnt diameter into the instantaneous measured value of diameter variations of diameter or linear density can be detected. Using the functions lr($\lambda$.n) and comparing the proportional contribution to the sum a measure of intensity in each band is obtained. This measurement is independent of the diameter. By employing a lowpass filter which approximates an definite integral function, a signal proportional to the running average of the proportional contribution of each band can be obtained. If the assumption is made that the fibre are mostly the correct colour, then this running average will learn the correct colour. By dividing this learnt colour into the instantaneous measured value of colour, variations of colour can be detected. By logical comparison of these variations of instantaneous measured diameter and colour to the learnt running average of diameter and colour, variation or diameter variation can be measured.

BRIEF DESCRIPTION OF DRAWINGS

FIGS. 5a, 6a and 7a are unscaled plots showing the proportion of signal that each of the detected red, blue and green bands contributed to the total signal depicted in FIG. 3 or 4.

DETAILED DESCRIPTION OF THE PREFERRED EMBODIMENTS

Figure 1:
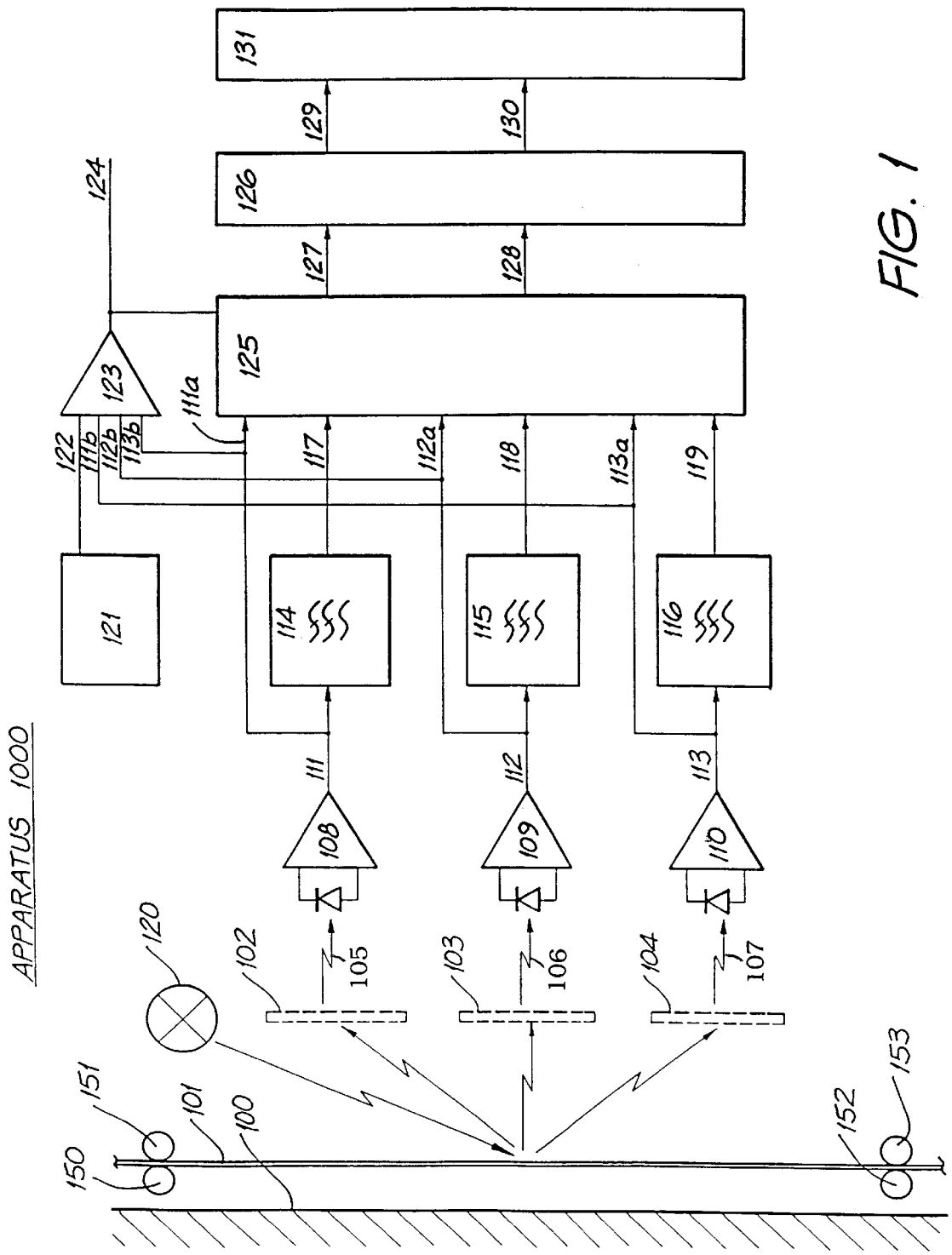
FIG. 1 is a block diagram of a first apparatus for determining a change in diameter and change in colour of a yarn.

In FIG. 1 an apparatus 1000 for determining a change in diameter and change in colour of a yarn 101 is depicted. Apparatus 1000 includes a light absorbing background 100 which generally comprises a flat black surface (or a flat matt black surface) to substantially uniformly absorb light falling thereon. Yarn guides 150 and 151 are adjacent to one another but are located a distance defining the measurement interaction volume, apart from yarn guides 152 and 153. Both sets of yarn guides 150 and 151 and 152 and 153 are disposed in close proximity to background 100 to locate and guide yarn 101 in such a way that when yarn 101 passes there between it does so in a direction which is substantially parallel to background 100 with the result that the distance between yarn 101 and background 100 is substantially constant. Light source 120 is located so as to direct a measurement light beam through the measurement interaction volume to interact with yarn 101 and thence to produce measurement outgoing light reflected from yarn 101.

Broad band width light source 120 is typically an incandescent tungsten filament globe. Filters 102, 103 and 104 are located relative to source 120 so as to spectral filter the reflected measurement outgoing light from the measurement interaction volume after interaction with yarn 101 into three measurement spectrally different wavelength bands 105, 106 and 107 respectively (for example filter 102 may pass 400–500 nm light, filter 103 may pass 500–650 nm light and filter 104 may pass 650–800 nm light).

Photodetectors 108, 109 and 110 are located behind filters 102, 103 and 104 respectively to respectively detect measurement spectrally different wavelength bands 105, 106 and 107 and to generate signals therefrom whereby the signals are a function of at least the diameter of the yarn and the colour of the yarn. Apparatus 1000 includes means for determining from the signals from photodetectors 108, 109 and 110 parameters which are functions of the diameter of yarn 101 and the colour of yarn 101. The means for determining includes temporal filters 114, 115 and 116, which are respectively coupled to photodetectors 108, 109 and 110 via lines 111, 112 and 113, signal processing unit 125 which is coupled to photodetectors 108, 109 and 110 via lines 111 and 111a, 112 and 112a, and 113 and 113a respectively, summing amplifier 123 which is coupled to photodetectors 108, 109 and 110 via lines 111, 111a and 111b, 112, 112a and 112b, and 113, 113a and 113b respectively and which is coupled to output line 124, reference voltage generator 121 which is coupled to summing amplifier 123 via line 122, and difference discriminator 126 having output lines 1.29 and 130 and which is coupled to signal processing unit 125 via lines 127 and 128. Line 124 is coupled to signal processing unit 125 via line 124x. Temporal filters 114, 115 and 116 are coupled to signal processing unit 125 vialines 117, 118 and 119 respectively. Lines 117, 118 and 119, lines 112, 112a and 112b, and lines 113, 113a, and 113b respectively carry electrical signals proportional to the current energy resulting from photodetection wavelength bands 105, 106 and 107. Lines 117, 118 and 119, respectively carry electrical signals corresponding to the running average energy resulting of wavelength bands 105, 106 and 107. Line 122 carries a reference voltage signal from reference voltage generator 121 to summing amplifier 123. Lines 124 and 124a carry all electrical signal proportional to the diameter of yarn 101. Line 127 carries an electrical signal corresponding to the colour variation in yarn 101. Line 128 carries an electrical signal corresponding to the diameter variation in yarn 101. Line 129 carries a digital electrical signal which is indicative of whether the measured colour variation of yarn 101 is acceptable or not. Line 130 carries a digital electrical signal which is indicative of whether the measured diameter variation of yarn 101 is acceptable or not. These digital electrical signals are passed to item 131 which is an external device to initiate the removal contaminate or colour faults.

In use yarn 101 is guided under tension by yarn guides 150 and 151 and 152 and 153 in a direction substantially parallel to background 100 Such that the distance between yarn 101 and background 100 is substantially constant. Yarn guides 150, 151, 152 and 153 define the measurement interaction volume in this embodiment of the invention. During the measurement, light source 120, filters 102, 103 and 104 and photodetectors 108, 109 and 110 are in fixed positions relative to background 100. Broad band light (e.g. 400–800 nm) emitted from source 120 is directed to yarn 101. Typically during the measurement, yarn 101 is moving so the measurement is a progressive one along its axis. The majority of light energy from source 120 is absorbed by background 100. A small part of the light energy from source 120 interacts with fibre 101 and is reflected back to the spectral filters 102, 103 and 104. Filter 102 passes a band of 400–500 nm light, filter 103 passes a band of 500–650 nm light and filter 104 passes a band of 650–800 nm light.

Photodetectors 108, 109, 110 respectively create electrical signals that are proportional to the energy reflected by yarn 101 in the respective bands. These three signals are sent to summing amplifier 123 via lines 111, 111a and 111b, 112, 112a and 112b, and 113, 113a and 113b, respectively. The three signals and a reference signal from reference voltage generator 121 via line 122 are summed by summing amplifier 123 to produce an electrical signal proportional to the measured diameter of yarn 101 in accordance with equation 1.9 which is output to lines 124 and 124a. The three signals are also passed to temporal filters 114, 115, 116 via lines 111, 112 and 113 respectively. These temporal filters approximate the definite integral used in the denominator of equation 1.10. Each of these filters output a signal corresponding to the running average of the energy reflected by yarn 101 in the respective bands. These latter signals are carried respectively on lines 117, 118, 119 to signal processing unit 125.

Signal processing unit 125 is composed of operational amplifiers and analogue dividers connected in such a fashion as to perform the functions described by equations 1.10, 1.11 and 1.12. Alternatively signal processing unit 125 may be connected to perform the functions described by equations 1.10, 1.12 and 1.13. Signal processing unit 125 takes the input signals from lines 111 and 111a, 112 and 112a, and 113 and 113a and running average signals from lines 117, 118 and 119 and combines these with the signal from line 124a to produce output signals via lines 127 and 128 which are respectively proportional to the difference between current and mean values of colour (line 127) and diameter (line 128). The processing to produce difference between current and mean values of diameter is done in accordance with equation 1.10 to produce a diameter variation signal which is output via line 128. The processing to produce difference between current and mean values of colour is done in accordance with equation 1.12 or 1.13 to produce a colour variation signal which is output via line 127.

Difference discriminator 126 consists of operational amplifiers and comparators and reference generators connected in such a manner so as to perform test described by equations 1.3 to 1.7. Difference discriminator 126 which processes the signals from lines 127 and 128 by comparison with the references, to output a digital electrical signal to line 129 which is indicative of whether the measured colour variation of yarn 101 is acceptable or not and output a digital electrical signal to line 130 which is indicative of whether the measured diameter variation of yarn 101 is acceptable or not. These digital electrical signals are passed to external device 131 to initiate corrective action.

Figure 2:
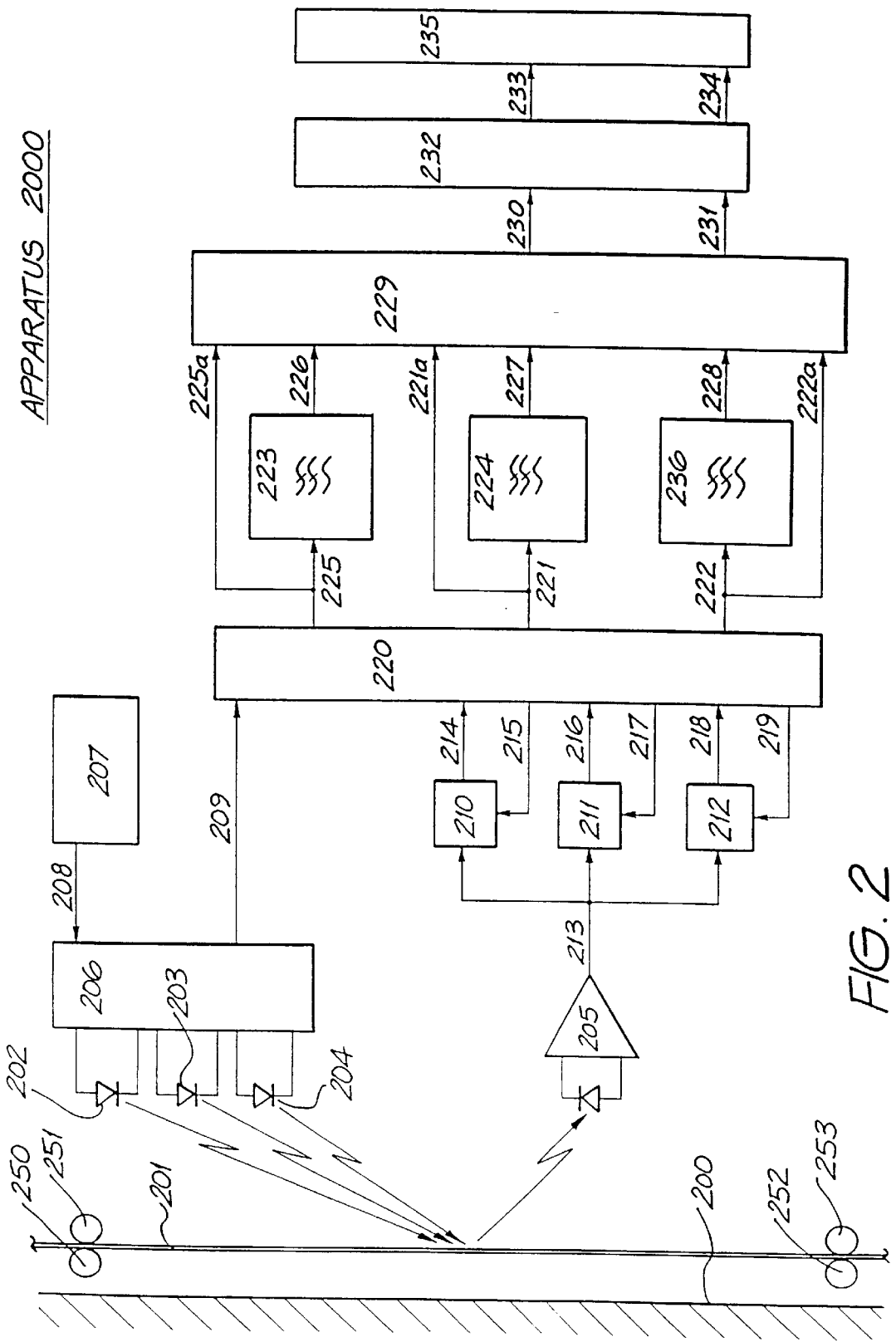
FIG. 2 is a block diagram of a second apparatus for determining a change in diameter and change in colour of a yarn.

In FIG. 2, an apparatus 2000 for determining a change in diameter and change in colour of a yarn 201 is depicted. Apparatus 2000 includes a light absorbing background 200 which generally comprises a flat black surface to substantially uniformly absorb light falling thereon. Yarn guides 250 and 251 are adjacent to one another but are located a distance defining the measurement interaction volume, apart from yarn guides 252 and 253. Both sets of yarn guides 250 and 251 and 252 and 253 are disposed in close proximity to background 200 to locate and guide yarn 201 in such a way that when yarn 201 passes there between it does so in a direction which is substantially parallel to background 200 with the result that the distance between yarn 201 and background 200 is substantially constant. A light source is located so as to direct a measurement light beam trough the measurement interaction volume to interact with yarn 201 and thence to produce measurement outgoing light reflected from yarn 201.

The light sources 202, 203 and 204 are typically light emitting diodes with differing predominant wavelengths in the visible spectrum. Their spectral bandwidth is such that the visible spectrum is covered with minimum overlap. These light sources are illuminated sequentially by sequencer 206 controlled by line 208 from oscillator 207. Line 209 connects to demodulating unit 220.

Detector 205 is located relative to sources 202, 203 and 204 so the reflected measurement outgoing light from the measurement interaction volume after interaction with yarn 201 is converted to an electrical signal carried on line 213. Line 213 connects sample and hold units 210, 211 and 212. Sample and hold units 210, 211 and 212 are controlled by lines 215, 217 and 219 respectively. Sample and hold units 210, 211 and 212 hold the detected signal on lines 214, 216 and 218 respectively.

Demodulation unit 220 controls sample and hold units 210, 211 and 212 via lines 215, 217 and 219 respectively. Demodulation unit 220 outputs lines 225, 221 and 222 to low pass filters 223, 224 and 225 respectively. Demodulation unit 220 also outputs lines 225a, 221a and 222a connected to signal processing unit 229. Signal processing unit 229 accepts signals on lines 225a, 221a 222a from demodulation unit 220. Signal processing unit 229 accepts signals on lines 226, a, 227 and 228 from low pass filters 223, 224 and 236 respectively. Signal processing unit outputs signal on lines 230, and 231 to discriminator 232. Discriminator unit 232 accepts signals on lines 230 and 231 from signal processing unit 229. External unit-235 accepts signal on lines 233 and 234 from discriminator unit 232 and signal on line 233 from signal processing unit 229 respectively.

In use yarn 201 is guided under tension by yarn guides 250 and 251 and 252 and 253 in a direction substantially parallel to background 200 such that the distance between yarn 201 and background 200 is substantially constant. During the measurement, light sources 202, 203 and 204 and sequentially illuminate yarn 201 with light from different bands of the visible spectrum. During measurement light sources 202, 203 and 204, detector 205 are in fixed positions relative to background 200. Typically during measurement yarn 201 is moving so the measurement is a progressive one along its axis. The majority of light energy from light sources 202, 203 and 204 is absorbed by background 200. A small part of the light energy from sources 202, 203 and 204 interacts with yarn 201 and is reflected back to detector 205.

Typically oscillator 207 is running at a frequency fast enough with respect to the speed of axial movement of yarn 201 so the samples of reflected light from each of the bands are essentially spatially 'coincident. Sequencer 206 is composed of a counter and decoder to give three discrete outputs that are mutually exclusive in time. These outputs typically drive three switches to sequence light sources 202, 203 and 204. Because the illumination of yarn 201 from light sources 202, 203 and 204 is sequential i.e., only one source is turned on for a fixed time before the next source is turned on, detector 205 converts the reflected spectral time series to an electrical time series on line 213. Sample and hold units 210, 211 and 212 sample this electrical time series and store a signal proportional to the reflected energy in a particular band. These signals for each band are available on lines 214, 216 and 218. Demodulator 220 under the control of sync signal on line 209, controls sample and hold 210, 211 and 212 on lines 215, 217 and 219 respectively. Demodulation unit 220 also contains operational amplifiers to compensate for signal and sensitivity at different parts of the visible spectrum. The signal outputs of demodulation unit 220 proportional to the energy reflected in each of the spectral band from yarn 201 are passed to low pass filters 223, 224 and 236 on lines 225, 221 and 222 respectively. These signals are also passed to signal processing unit 229 on lines 225a, 221a and 222a respectively.

Low pass filters 223, 224 and 236 approximate the definite integral function used in the denominator of equation 1.13. Signal processing unit 229 is composed of operational amplifiers and analogue dividers connected in such a fashion as to perform the functions described by equations 1.9, 1.10, 1.11 and 1.12. Alternatively signal processing unit 229 may be connected to perform the functions described by equations 1.9, 1.10, 1.12 and 1.13. The signals proportional to parameters of colour and diameter are passed from signal processing unit 229 to discriminator unit 232 on lines 230 and 231 respectively.

Difference discriminator 232 consists of operational amplifiers and comparators and reference generators connected in such a manner so as to perform test described by equations 1.3 to 1.7. Difference discriminator 232 which processes the signals from lines 230 and 231 by comparison with the references, to output a digital electrical signal to line 233 which is indicative of whether the measured colour variation of yarn 201 is acceptable or not and output a digital electrical signal to line 234 which is indicative of whether the measured diameter variation of yarn 201 is acceptable or not. These digital electrical signals are passed to external device 131 to initiate corrective action.

EXAMPLE 1

Figure 3:
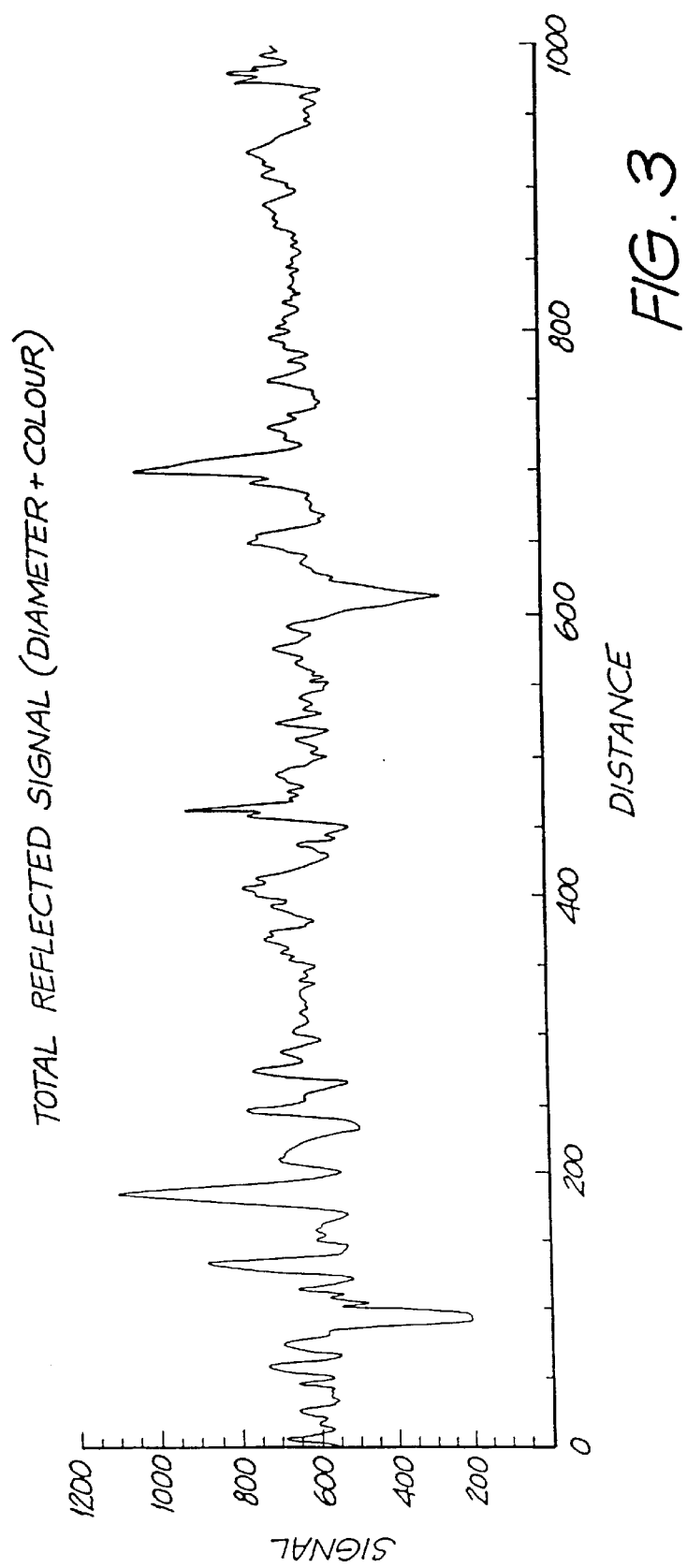
FIG. 3 is a plot of the signal taken from line 124 (of the apparatus of FIG. 1)
Figure 4:
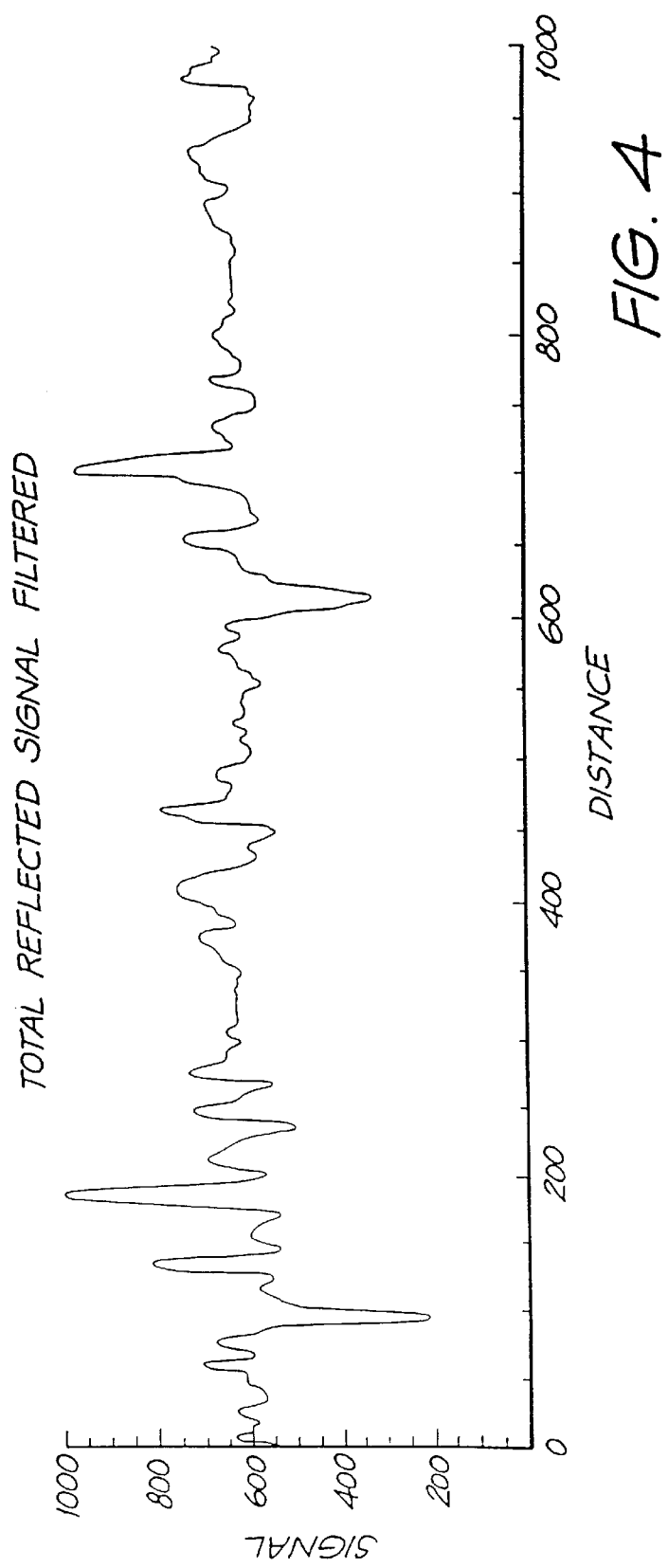
FIG. 4 is a plot of the signal taken from line 124 (of the apparatus of FIG. 1) after temporal filtering.
Figure 5:
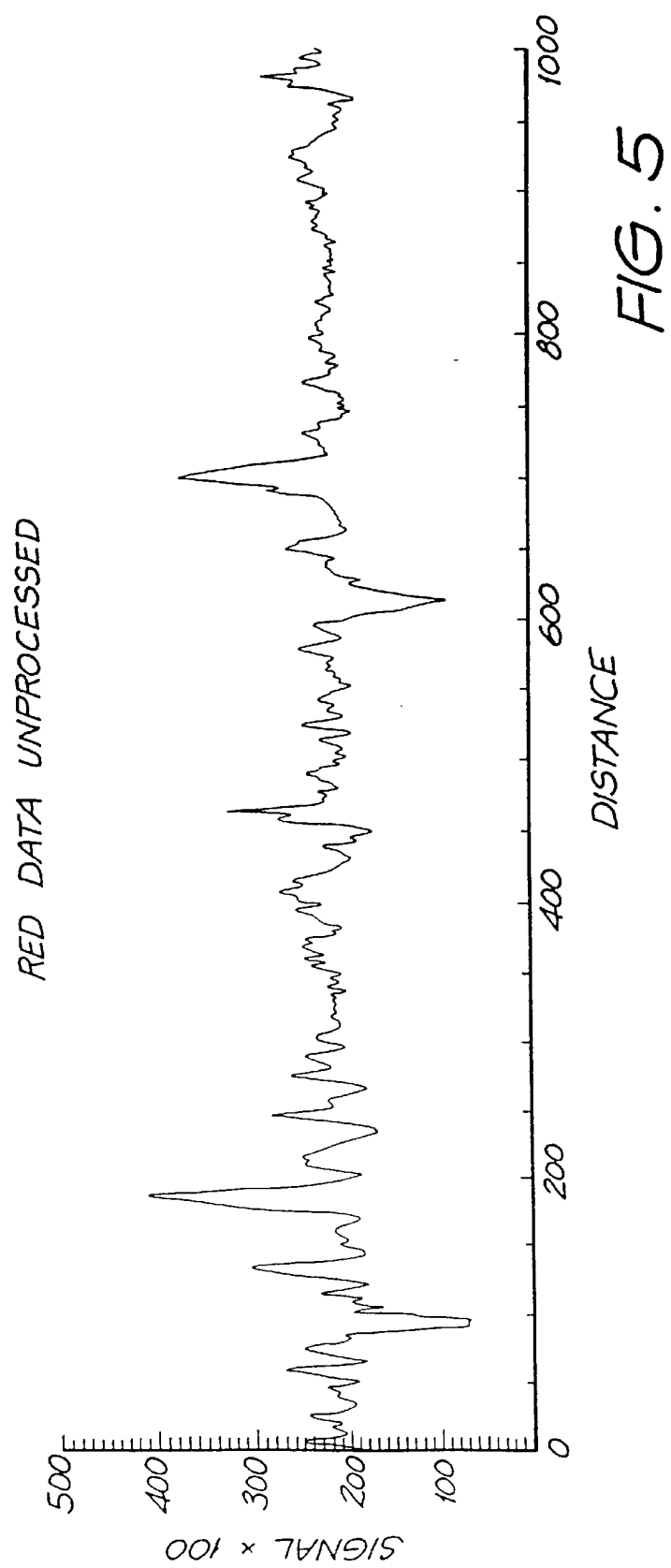
FIGS. 5, 6 and 7 are plots of the signals taken from lines 111, 112 and 113 (of the apparatus of FIG. 1) respectively.
Figure 6:
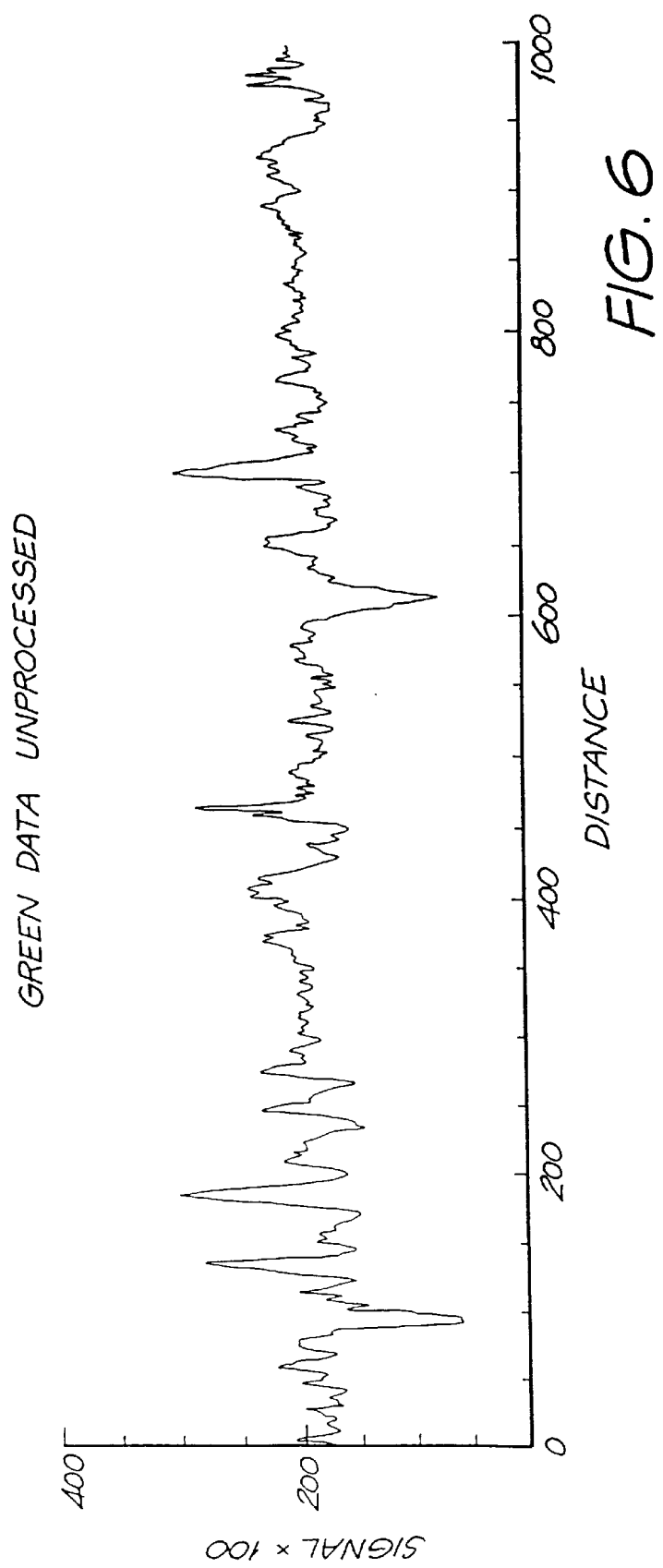
Figure 6A:
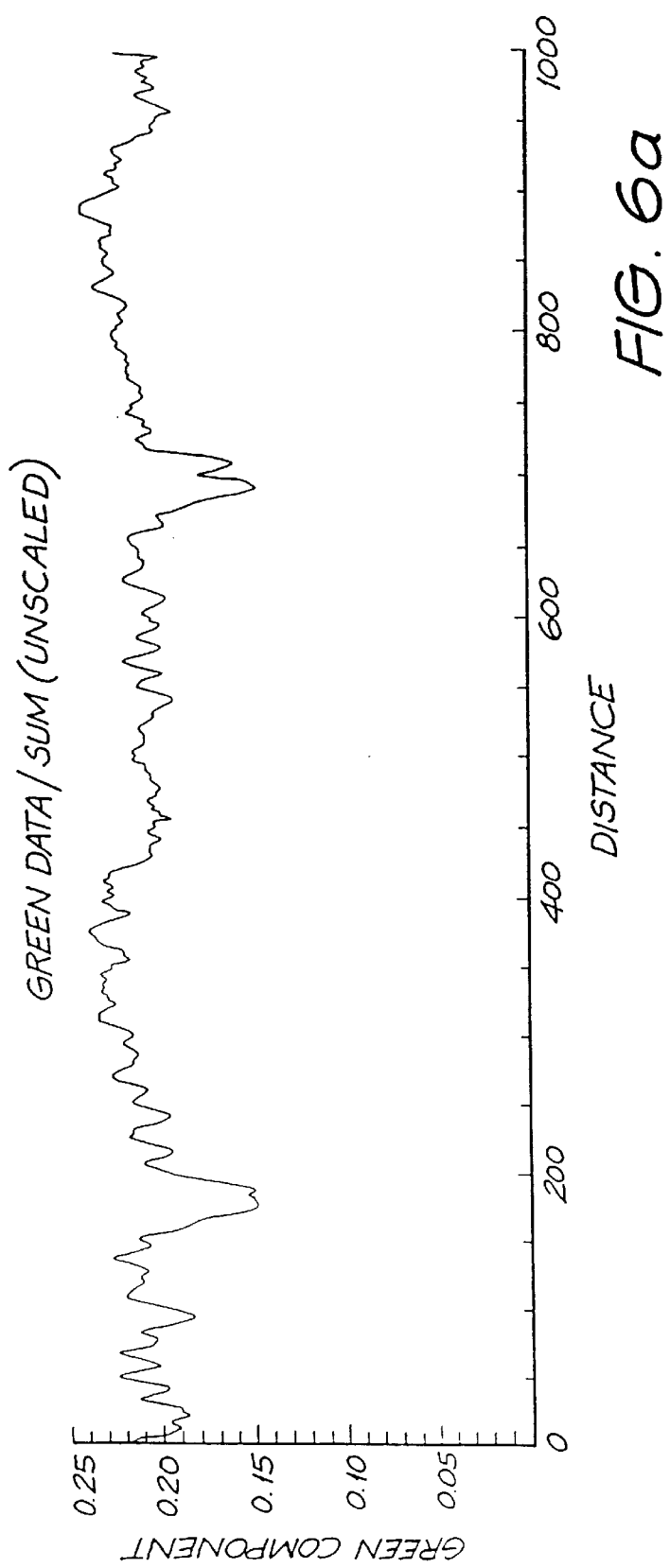
Figure 7:
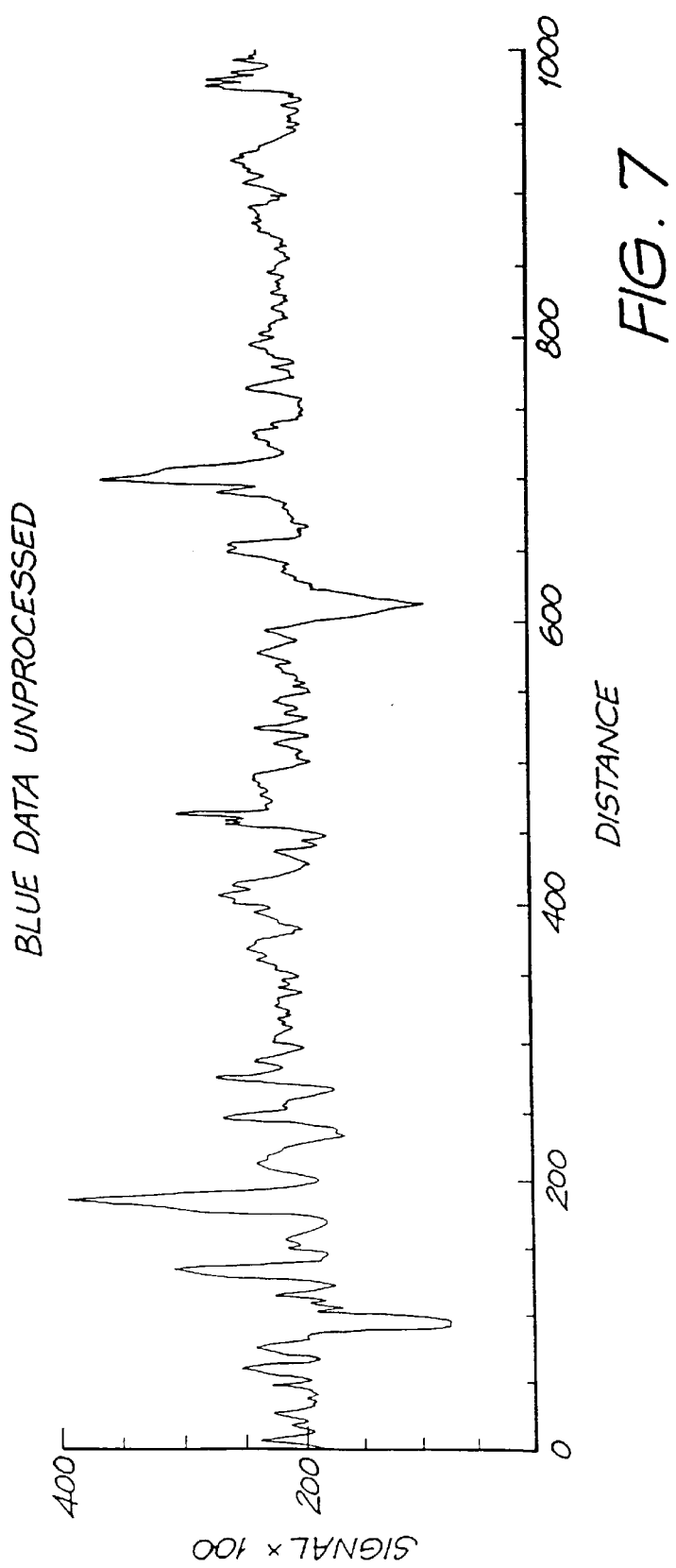
Figure 7A:
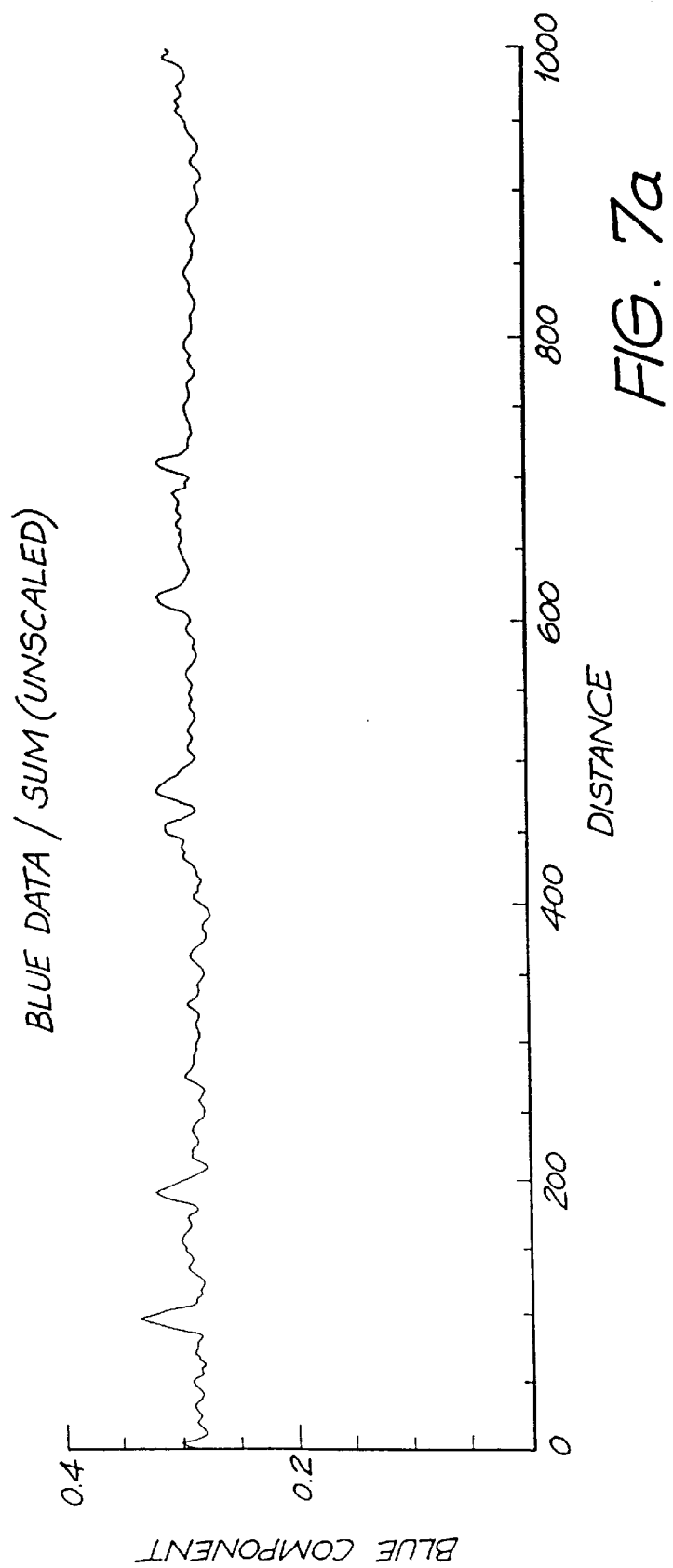

An experiment using the configuration of FIG. 1 was conducted on a white yarn (yarn formed from natural wool fibre with diameter variation at various positions along the yarn and having fibres of various non white colours twisted through the white yarn at various positions along the yarn. FIG. 3 is a plot of the signal taken from line 124 (of the apparatus of FIG. 1) which signal corresponds to the sum of reflected light detected. FIG. 4 is a plot of the signal taken from line 124 (of the apparatus of FIG. 1) after temporal filtering, which temporally filtered signal corresponds to the sum of reflected light detected. FIGS. 5, 6 and 7 are plots of the signals taken from lines 111, 112 and 113 (of the apparatus of FIG. 1) respectively. Typically, these signals respectively correspond to the detected light after spectral filtering to give signals corresponding to detected red, detected green and detected blue light bands respectively. FIGS. 5a, 6a and 7a are unscaled plots showing the proportion of signal that each of the detected latter bands contributed to the total signal depicted in FIG. 3 or 4. By comparing the proportional energy in each band at a particular point along the yarn, where a white yarn is being measured, to that in other bands, at the same particular point, a "signature" of the white colour can be obtained. One example of this has been given in Equation 1.11. By integrating equation 1.11 over a significant area (period of time t1 ... t2) of the fibre one can obtain a value of the "normal" colour of the fibre. By dividing this normal value into the instantaneous value one can obtain a signal which is independent of the illumination intensity and fibre diameter. If the current area being measured is "normal" white colour then this ratio approximates unity and is stable. If one gets a colour variation this ratio will vary from unity by an amount proportional to the size of the colour variation.

By comparison of this variation to a settable reference, an output signal can be generated that will indicate if a colour fault exists.

EXAMPLE 2

Figure 8:
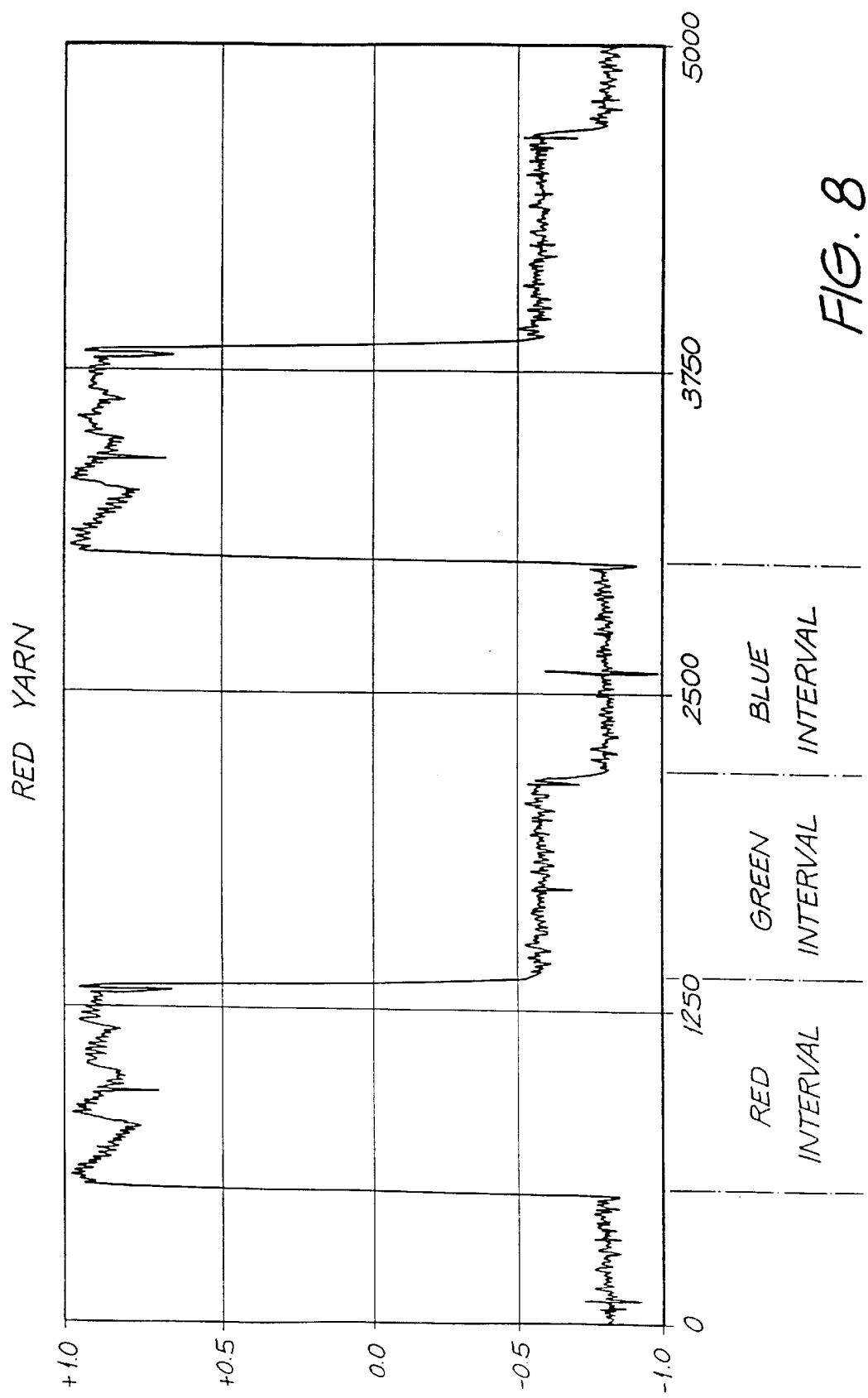
FIGS. 8, 9 and 10 are plots of the signals taken from line 213 (which carries the signal corresponding to the temporal sequence of reflected light energy) in an experiment using the configuration of FIG. 2 showing the sequence of colour variation on red, yellow and blue yarns respectively.
Figure 9:
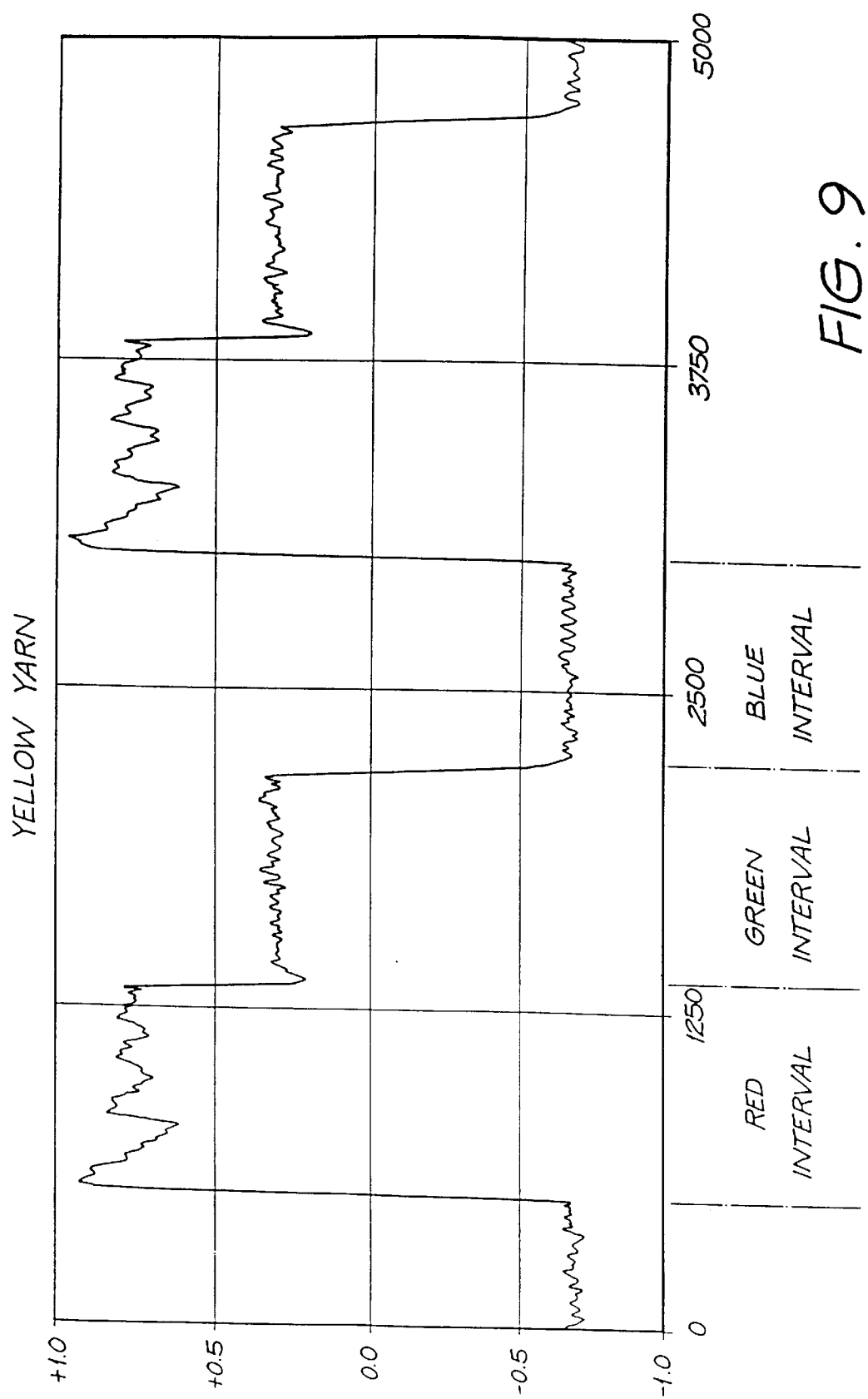
Figure 10:
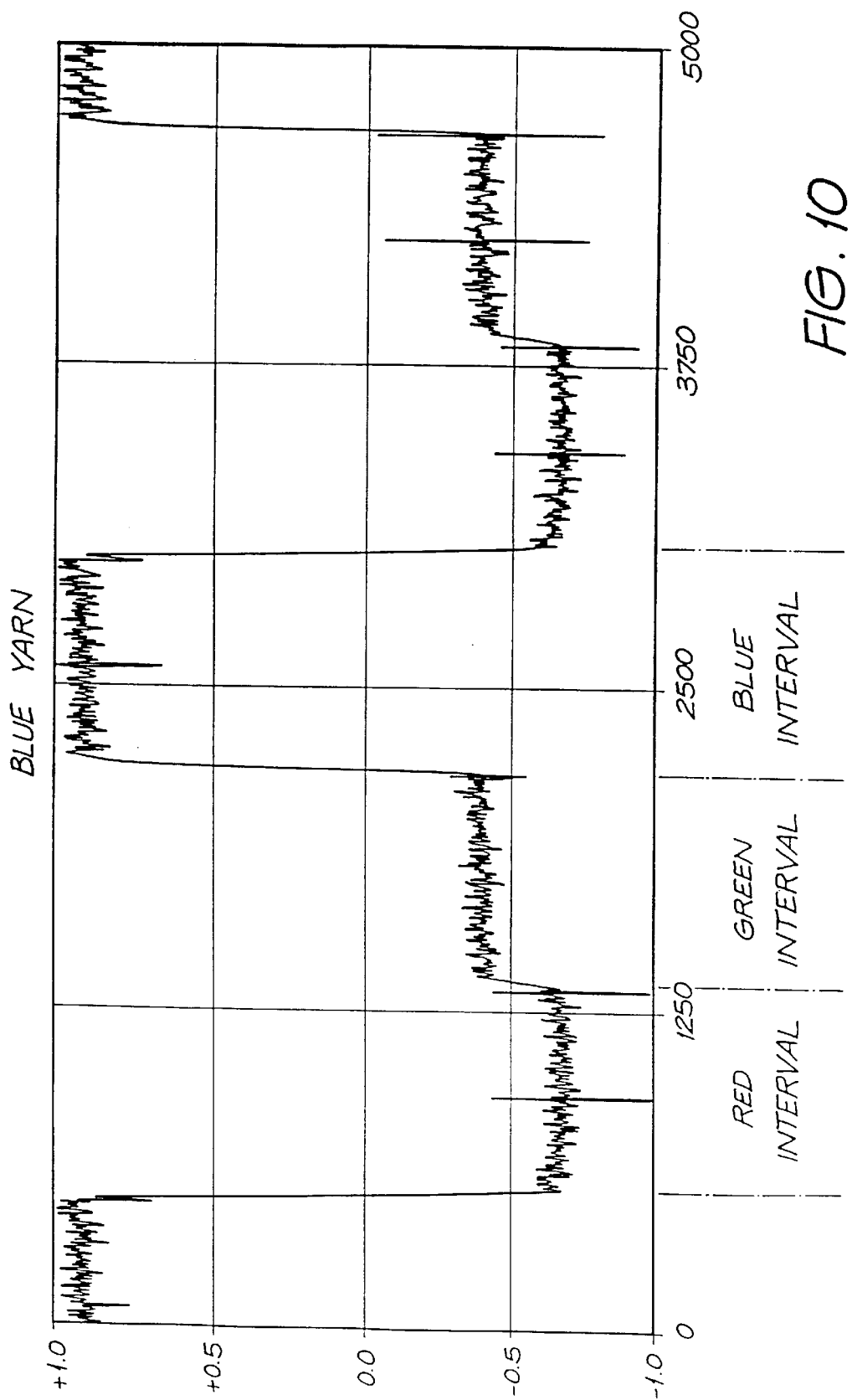

An experiment using the configuration of FIG. 2 was conducted on red, yellow and blue yarns respectively. FIGS. 8, 9 and 10 are plots of the signals taken from line 213 (which carries the signal corresponding to the temporal sequence of reflected light energy) showing the sequence of colour variation on red, yellow and blue yarns respectively.

What is claimed is:

1. An apparatus for determining at least a first measurement parameter of an object, comprising:
    means for locating the object in a measurement interaction volume;
    at least one light source for passing a measurement light beam through the measurement interaction volume to interact with the object to produce measurement outgoing light, the measurement light beam comprising at least two spectrally different wavelengths of light;
    at least one detector to detect portions of the at least two measurement spectrally different outgoing light and to generate signals therefrom, whereby the signals are a function of the at least first measurement parameter, the detector being operatively associated with the light source;
    means for filtering the measurement outgoing light from the measurement interaction volume into at least two measurement spectrally different outgoing light portions, the means for filtering being operatively associated with at least one of the light source and the at least one detector; and
    means for determining the at least first measurement parameter from the signals, the means for determining being operatively associated with the detector, and
    a light absorbing background operatively associated with the measurement interaction volume and the at least one detector such that said at least one detector receives substantially only measurement outgoing light directly reflected from said object.

2. Apparatus according to claim 1 wherein the light absorbing background is a black background.

3. Apparatus according to claim 1 wherein the light absorbing background is a matt black background.

4. Apparatus according to claim 1 or 3 wherein the light absorbing background is a flat background.

5. An apparatus according to claim 1, wherein said apparatus includes at least two detectors, said at least two detectors permitting each measurement spectrally different outgoing light portion to be detected by a different detector at the same time or at different times, and generating signals therefrom whereby the signals are a function of the at least first measurement parameter.

6. The apparatus of claim 1 wherein, said means for filtering is one of means for spectral filtering and means for temporal filtering.

7. The apparatus of claim 1, further comprising:

means for outputting a first parameter signal which is a function of the first, the means for outputting being operatively associated with means for determining the at least first measurement parameter.

8. The apparatus of claim 5, further comprising:

means for outputting a first parameter signal which is a function of the at least first measurement parameter, the means for outputting being operatively associated with the means for determining the at least first measurement parameter.

9. The apparatus of claim 5, 6, 7 or 8, further comprising:

means for determining from at least first measurement parameter whether the object satisfies preselected acceptance conditions, the means for determining being operatively associated with the means for determining the at least first measurement parameter.

10. The apparatus of any one of claim 1, 2, 3, 4, 5, 6, 7 or 8, wherein the at least first measurement parameter is or is a function of at least one parameter which is one of a diameter of a yarn, a diameter of a fibrous object, a color of a fibrous object and a color of a yarn.

11. The apparatus of claim 1, 2, 3, 4, 5, 6, 7 or 8, wherein the object is one of a fiber and a yarn, and the at least first measurement parameter is one of a diameter of the fiber, a difference between the diameter of the fiber and a diameter of a reference fiber, a ratio of an instantaneous diameter of the fiber divided by a running average diameter of the fiber, a color of the fiber, a difference between the color of the fiber and a color of a reference fiber, a ratio of an instantaneous color of the fiber divided by a running average color of the fiber, a diameter of the yarn, a difference between the diameter of the yarn and a diameter of a reference yarn, a color of the yarn, a ratio of an instantaneous color of the yarn divided by a running average color of the yarn, and a difference between the color of the yarn and the color of the reference yarn.

12. The apparatus of claim 1, 2, 3, 4, 5, 6, 7 or 8, wherein the object is one of a diameter of wool fiber, a difference between a diameter of the wool fiber and a diameter of a reference fiber, a ratio of an instantaneous diameter of the wool fiber divided by a running average diameter of the wool fiber, a color of the wool fiber, a difference between the color of the wool fiber and a color of a reference fiber, a ratio of an instantaneous color of the wool fiber divided by a running average color of the wool fiber, a diameter of the wool yarn, a difference between a diameter of the wool yarn and a diameter of a reference yarn, a ratio of an instantaneous diameter of the wool yarn divided by a running average diameter of the wool yarn, a color of the wool yarn, a ratio of an instantaneous color of the wool yarn divided by a running average color of the wool yarn, and a difference between the color of the wool yarn and a color of a reference yarn.

* * * * *